United States Patent
Greller et al.

(10) Patent No.: US 8,870,443 B2
(45) Date of Patent: Oct. 28, 2014

(54) FLEXIBLE POUCH WITH A MIXING APPARATUS

(75) Inventors: Gerhard Greller, Goettingen (DE); Guenter Pradel, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 955 days.

(21) Appl. No.: 12/933,453

(22) PCT Filed: Mar. 27, 2009

(86) PCT No.: PCT/EP2009/002281
§ 371 (c)(1),
(2), (4) Date: Sep. 20, 2010

(87) PCT Pub. No.: WO2009/143925
PCT Pub. Date: Dec. 3, 2009

(65) Prior Publication Data
US 2011/0026360 A1 Feb. 3, 2011

(30) Foreign Application Priority Data
Apr. 17, 2008 (DE) .......................... 10 2008 019 213

(51) Int. Cl.
*B01F 7/16* (2006.01)
*B01F 13/06* (2006.01)
*B01F 15/00* (2006.01)
*C12M 1/06* (2006.01)
*F16C 3/03* (2006.01)
*B01F 7/00* (2006.01)
*C12M 1/00* (2006.01)
*B01F 7/22* (2006.01)

(52) U.S. Cl.
CPC ......... *B01F 7/00633* (2013.01); *B01F 15/0085* (2013.01); *C12M 27/02* (2013.01); *B01F 15/00831* (2013.01); *F16C 3/03* (2013.01); *B01F 7/007* (2013.01); *C12M 23/14* (2013.01); *B01F 7/00716* (2013.01); *B01F 7/00691* (2013.01); *B01F 7/22* (2013.01)
USPC .......................................... 366/102; 366/286

(58) Field of Classification Search
CPC ........... B01F 15/00831; B01F 15/0085; B01F 7/0063; B01F 7/161
USPC .................................. 366/101, 102, 285, 286
See application file for complete search history.

(56) References Cited

U.S. PATENT DOCUMENTS 3,202,281 A * 8/1965 Weston .......................... 366/101
3,246,882 A    4/1966 Clough
3,357,685 A * 12/1967 Stephens ....................... 366/282

(Continued)

FOREIGN PATENT DOCUMENTS

DE  20 2007 005 868    8/2007
EP    1 541 224         6/2007

(Continued)

OTHER PUBLICATIONS

International Preliminary Report on Patentability, PCT/EP2009/002281, 13 pages total.

*Primary Examiner* — Tony G Soohoo
(74) *Attorney, Agent, or Firm* — Gerald E. Hespos; Michael J. Porco; Matthew T. Hespos

(57) ABSTRACT

A flexible pouch has a mixing apparatus, the mixer shaft of which is adjustable in length for use as a bioreactor for culturing microorganisms and cells.

15 Claims, 2 Drawing Sheets

(56) References Cited

U.S. PATENT DOCUMENTS

| | | | |
|---|---|---|---|
| 5,078,506 A * | 1/1992 | Tischer | 366/314 |
| 5,765,947 A | 6/1998 | Dubroy | |
| 5,906,543 A | 5/1999 | Jones | |
| 2006/0230865 A1 | 10/2006 | Castellon | |
| 2010/0260010 A1 * | 10/2010 | Jornitz | 366/343 |

FOREIGN PATENT DOCUMENTS

| | | | | |
|---|---|---|---|---|
| GB | 2 195 441 | | 4/1988 | |
| JP | 6-285353 | * | 4/1993 | ............... B01F 7/16 |
| JP | 6-285353 | | 10/1994 | |
| WO | WO 2009077125 | * | 6/2009 | ............... B01F 7/18 |
| WO | WO 2013151733 | * | 10/2013 | |

* cited by examiner

FLEXIBLE POUCH WITH A MIXING APPARATUS

BACKGROUND OF THE INVENTION

1. Field of the Invention

The invention relates to a flexible pouch with a mixing apparatus, the mixer shaft of which is adjustable in length, in particular for use as a bioreactor for culturing microorganisms and cells or as a mixing apparatus for media or for dissolving or suspending substances in fluids, such as for instance for producing buffer solutions.

2. Description of the Related Art

Bioreactors in which the culture medium is accommodated in flexible pouches of polymer material are obtainable over a range of volumes extending from a few liters to several hundred liters. In the case in particular of large-volume pouches, there are problems with thorough mixing of the culture medium, which is intended to ensure a uniform oxygen partial pressure. Thorough mixing is very often carried out using rotating stirring rods which consist of a mixer shaft and one or more stirring elements, such as for example propellers, and which are introduced into the interior of the pouch. Stirring elements also exist in the form of paddles or vertically vibrating mixer plates. Since with a single-use bioreactor all the parts which come into contact with cells during culturing may ideally be discarded, it is advantageous to make the mixer shaft of favorable plastics material too.

When it comes to the storage and transport of single-use bioreactors with a volume of 200 to 1000 liters, the mixer shaft, unlike the pouch, which may be folded and compressed, constitutes a problem, since its length easily exceeds the size of common packaging and storage units.

After culturing, it may also be advantageous to reduce the size of the pouch again, for example if the cell-containing culture medium is to be cooled and stored. In this case the gas located in the headspace of the pouch could be expelled, whereby the height of the pouch could as a rule be reduced by a third, which would however require a length-adjustable mixer shaft. A similar problem arises if the cells or microorganisms contained in the pouch are to be killed by heat after an abortive attempt at culturing, and the mixer shaft proves too bulky for the autoclave.

It is known from German patent application 10 2006 021 984 A1 to assemble a mixer shaft from a plurality of separate parts, with the objective of being able to equip bioreactors of different sizes with standard mixer components. It would in principle also be possible, in order to reduce the storage and transport height of the pouch, to deliver the mixer shaft in a plurality of individual parts, as described in DE 10 2006 021 984 A1, and only to assemble the mixing apparatus before it is brought into operation. However, this approach is thwarted by the fact that on delivery the separate mixer shaft parts are already presterilized inside the sterile pouch and therefore could not really be assembled into the mixer shaft without opening the sterile interior of the pouch.

The object of the invention is therefore to propose a flexible pouch with a mixing apparatus, the mixer shaft of which may be simply converted from a short transport/storage length into an extended operating length in the sterile interior of the pouch, without the sterile envelope of the bioreactor having to be opened in the process, or which may be reduced back down to its original transport/storage length without the pouch having to be opened in the process.

SUMMARY OF THE INVENTION

The object is achieved according to the invention by a length-adjustable mixer shaft. The invention comprises a flexible pouch with a mixing apparatus, which comprises a length-adjustable mixer shaft, which is subdivided into at least two or a plurality of shaft elements, a first one of two adjacent shaft elements comprising a hollow member in which is displaceably accommodated a filler member of the second shaft element.

At least the two outer shaft elements are here closed on the side facing the pouch.

The hollow members of a first one of two adjacent shaft elements and the filler member of the second shaft element comprise a common, continuous circumferential contour, with circular, oval or polygonal contours being preferred.

In a preferred embodiment, at least one resilient element is located between the hollow member of the first shaft element and the filler member of the second shaft element, the at least one resilient element preferably consisting of two spaced rings, which may be made for example of a plastics material, such as rubber or silicone. For fastening purposes, the two spaced rings may be partially let into a groove, which is located on the filler member of the second shaft element or in the hollow member of the first shaft element, or be formed on the filler member of the second shaft element or on the hollow member of the first shaft element by multi-, in particular 2-component injection molding technology.

In the case of a circular embodiment of the hollow member and of the filler member, on rotation of the mixer shaft the at least one resilient element transmits torque between the hollow member of the first shaft element and the filler member of the second shaft element, the transmitted torque preferably amounting to 0 to 50 Nm.

A further function of the at least one resilient element consists in sealing off the cavity in the interior of the mixer shaft against fluids from the interior of the pouch, the cavity in the interior of the mixer shaft being connected to the interior of the pouch by a duct which allows pressure equalization. In a preferred embodiment, the duct for pressure equalization connects the cavity in the interior of the mixer shaft with the gas-filled headspace in the pouch. In a modified embodiment, the duct may be sealed off against fluids by a microporous, hydrophobic membrane.

In a further embodiment, each of the shaft elements may be equipped with at least one stirring element.

To lock the mixer shaft in a specific position, the hollow member and/or the filler member may comprise a groove, in which one of the resilient elements seated in a groove or formed by 2-component technology may be engaged.

In principle many variants are feasible for performing length adjustment of the mixer shaft in a bioreactor. Assuming that the mixer shaft may only be manipulated indirectly via the relatively rigid envelope of the pouch (as explained with regard to the problem addressed), it has proven particularly advantageous to make the connection between the shaft elements telescopic, a first of two adjacent shaft elements comprising a hollow member in which a filler member of a second shaft element is accommodated in longitudinally displaceable manner. Length adjustment may be simply performed in particular when the mixer shaft is continuous, i.e. when the first end of the mixer shaft is mounted at the top and the second end at the bottom in the pouch, with the ends being capable of providing purchase for the length adjustment.

It has proven particularly favorable to introduce at least one resilient element in the gap between the hollow member of a first one of two adjacent shaft elements and the filler member of the second shaft element. This at least one resilient element here consists preferably of two spaced rings, which may be made of a plastics material such as for instance rubber. The rings assume two important functions for connecting the hollow member to the filler member: firstly, they ensure, through close contact with the filler member and with the hollow member, that the torque of the rotating mixer shaft is transmitted between the hollow member and the filler member and thus between the two shaft elements. Secondly the hollow member of the first shaft element is sealed by the rings against fluids from the interior of the pouch. This is particularly important, since a cavity forms in the mixer shaft when the filler member is extended, which in the absence of sealing would fill with culture medium and dying cells, which could have a negative effect on the overall culture.

The use of a resilient element, for example in the form of rings, additionally has the considerable advantage that locking of the mixer shaft at a desired length is ensured just by the frictional force acting between the hollow member, the resilient element and the filler member. When resilient elements are used, it is therefore possible to dispense with other locking mechanisms, for instance ball catches, which comprise metallic components. This is associated with advantages because, if the pouch is to be sterilized with gamma radiation, the metallic components could shield microbes from the radiation.

The cross-section of the hollow member and of the filler member may in principle assume a plurality of forms, with circular hollow members and filler members having the advantage that they are easy to manufacture and its being significantly easier to seal the hollow member of the first shaft element with round resilient elements than with non-circular embodiments.

Non-circular hollow members and filler members have the advantage, on the other hand, that the torque arising during stirring may be transmitted between the two shaft elements merely as a result of their shapes being latched together.

The resilient element is preferably fixed in place by introducing a groove into the filler member or into the hollow member, into which groove the resilient element is partially let in. Alternatively the resilient element may also be attached by 2-component technology to the filler member the hollow member.

To lock the mixer shaft at a given length, one of the rings located on the filler member may be engaged in a groove, which is incorporated into the inner side of the hollow member.

The use of at least one resilient element between the first and second shaft elements is a preferred solution specifically for circular hollow members and filler members, since the stirring rod torque which has to be applied for thorough mixing of a single-use bioreactor is not as a rule very great. This means that the frictional force acting between the rings and the two shaft elements for the purpose of stirring likewise does not have to be very great. If the frictional force is adjusted by way of the contact pressure of the rings to be of precisely such a magnitude that the maximum torque needed for stirring may be transmitted, the frictional force which arises during the longitudinal displacement occurring during length adjustment is also relatively slight and may as a rule be manually overcome (cf. exemplary embodiment 1).

In other words, rings with a suitably selected contact pressure on the one hand allow the longitudinal displacement of the shaft elements needed for length adjustment with moderate effort while on the other hand preventing radial sliding of the rings on the hollow member or the filler member during stirring.

Furthermore, the rings also perform an important sealing function, by preventing culture medium from the interior of the pouch from penetrating into a cavity of the mixer shaft. This cavity is present at least when the mixer shaft is extended. In this case the cavity comprises at least a part of the hollow member of a first one of two adjacent shaft elements, from which the filler member of the second shaft element has been partially withdrawn. The cavity inside the mixer shaft may also extend over a plurality of shaft elements, for example if the filler member of the second of two adjacent shaft elements is in turn of hollow construction. The seal prevents a dead volume filled with culture medium and dying cells from forming in the cavity, which could have a negative effect on the culture overall.

Because of the cavity inside the mixer shaft being sealed by the rings, or another kind of resilient element, it must nevertheless be ensured that pressure equalization takes place when the shaft is extended, since otherwise a vacuum would develop inside the mixer shaft, which would force the extended shaft elements back into their starting position. This pressure equalization is ensured according to the invention by gas flowing into the cavity of the mixer shaft. This gas feed proceeds via a duct, which preferably connects the cavity with the gas-filled headspace of the bioreactor. Another solution, in which the duct connects the cavity inside the mixer shaft with a gas volume outside the pouch, is also conceivable, but there is then a risk of contamination of the pouch interior. The duct preferably comprises a hydrophobic filter permeable to gases but impermeable to microorganisms and cells relative to the headspace of the pouch or relative to the gas volume outside the pouch.

A significant advantage of the present invention consists in the fact that the mixer shaft is continuously adjustable. The mixer shaft may thus be used for bioreactors of the most varied sizes. In addition, the avoidance of small mechanical parts such as ball catches, in particular those of metal, constitutes an advantage because, if the pouch is to be sterilized with the assistance of gamma radiation, any metal part could shield microbes from the radiation.

The following Figures and examples explain the invention in greater detail.

DETAILED DESCRIPTION OF THE PREFERRED EMBODIMENTS

Figure 1:
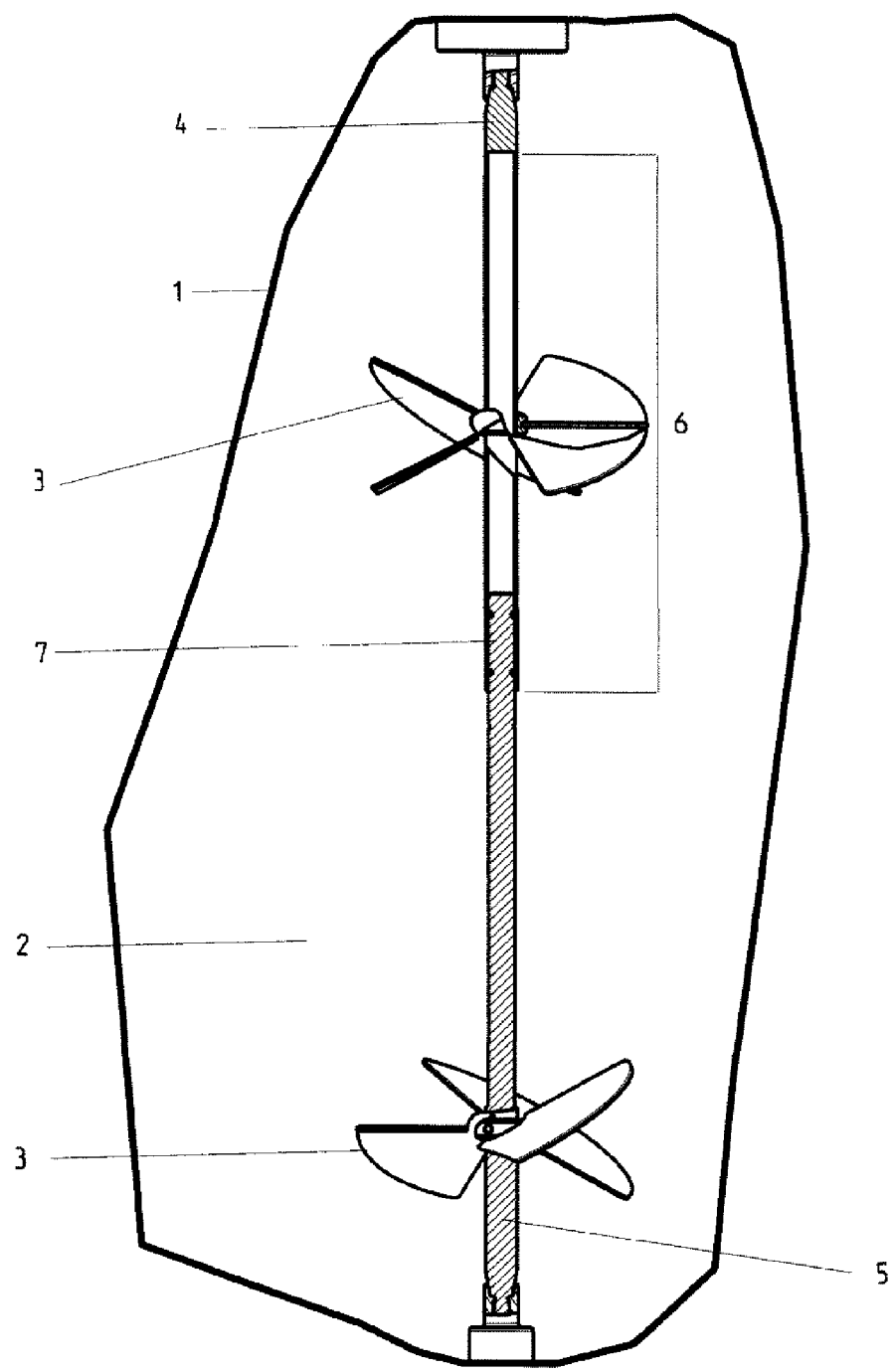
FIG. 1 shows an overview of the pouch with mixing apparatus.

According to FIG. 1 the pouch 1 has an interior 2, which accommodates a stirring rod consisting of two stirring elements 3 and a mixer shaft. The mixer shaft consists of a first shaft element 4 and a second shaft element 5. The first shaft element here comprises a hollow member 6, in which is displaceably mounted a filler member 7 of the second shaft element.

Figure 2:
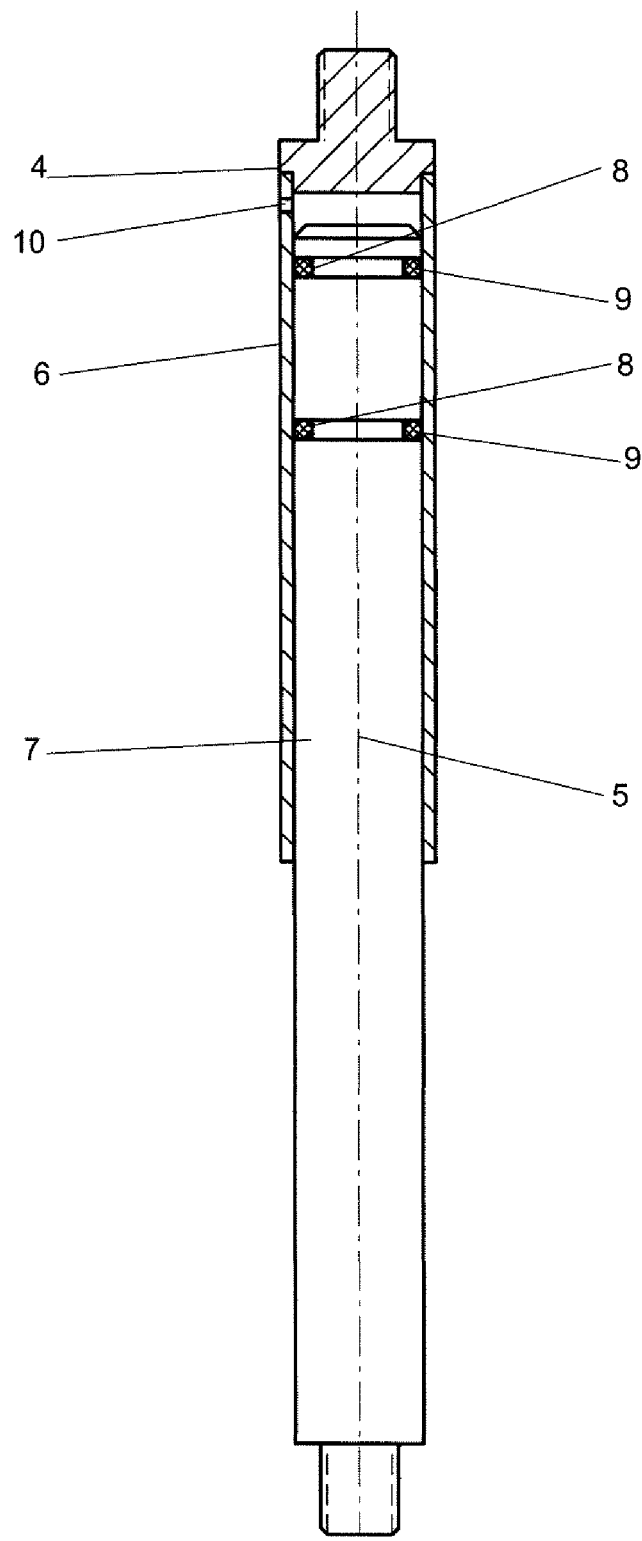
FIG. 2 shows the connection of two shaft elements in detail.

According to FIG. 2 two grooves 8 are incorporated into the first shaft element 4, a ring 9 being let into each of said grooves. In the hollow member 6 of the first shaft element 4 there is located a duct 10, which connects the cavity of the hollow member with the interior 2 of the pouch. The connection is preferably covered with a hydrophobic filter permeable to gases and impermeable to microorganisms and cells, which filter is sealed over the opening (not shown).

Exemplary Embodiment 1

Two O-rings with a radius of 1 cm are intended to transmit a torque of at most 5 Nm. The frictional force $F_R$ necessary therefor between the O-rings, the hollow member and the filler member results from the maximum torque $M_m$, and the O-ring circumference U.

$$U = 2r\pi = 0.0628 \text{ m}$$

$$F_r = M_m/U = 5 \text{ Nm}/0.0628 = 81 \text{ N}$$

A force of approx. 80 N is accordingly sufficient to overcome the frictional force of the O-rings and perform length adjustment of the mixer shaft; a force which may be readily applied manually or by means of simple mechanical devices.

The invention claimed is:

1. A flexible pouch (1) with a mixing apparatus, comprising:
a length-adjustable mixer shaft divided into at least first and second shaft elements (4, 5), the first shaft element (4) having a hollow body (6), the second shaft element (5) having a filler body (7) displaceably received in the hollow body (6) of the first shaft element (4), at least one resilient element (9) disposed in a gap between the hollow body (6) of the first shaft element (4) and the filler body (7) of the second shaft element (5), and a duct (10) being formed through a wall of the hollow body (6) and connecting a closed cavity of the mixer shaft to an interior (2) of the flexible pouch (1) achieve pressure equalization between the closed cavity and the interior (2) of the flexible pouch (1).

2. The flexible pouch of claim 1, wherein ends of the first and second shaft elements are (4, 5) closed at ends facing walls of the pouch (1).

3. The flexible pouch of claim 1, wherein the hollow member (6) and the filler member (7) of the at least first and second shaft elements (4, 5) comprise a form-fitting, interlocking circumferential contour.

4. The flexible pouch of claim 3, wherein the hollow member (6) and the filler member (7) of the at least first and second shaft elements (4, 5) are of circular construction.

5. The flexible pouch of claim 4, wherein the hollow member (6) and the filler member (7) of the at least first and second shaft elements (4, 5) are of polygonal or oval construction.

6. The flexible pouch of claim 1, wherein the at least one resilient element (9) is made from a plastics material, such as rubber or silicone.

7. The flexible pouch of claim 1, wherein at least one of the hollow member (6) and the filler member (7) is formed with a groove (8) and the at least part of the at least one resilient element (9) being engaged in the groove (8).

8. The flexible pouch of claim 1, wherein the at least one resilient element (9) is formed on the filler member (7) of the second shaft element (5) or on the hollow member (6) of the first shaft element (4) by 2-component technology.

9. The flexible pouch of claim 1, wherein the at least one resilient element (9) comprises two spaced rings.

10. The flexible pouch of claim 9, wherein the at least one resilient element (9) is dimensioned and configured to engage both the hollow member (6) and the filler member (7) sufficiently to transmit a torque between the hollow member (6) of the first shaft element (4) and the filler member (7) of the second shaft element (5) in response rotation of one of the shaft elements (4, 5) of the mixer shaft.

11. The flexible pouch of claim 10, wherein the engagement of the at least one resilient element (9) with the hollow member (6) and the filler member (7) is sufficiently secure to transmit a torque of between 0 and at least 50 Nm.

12. The flexible pouch of claim 1, wherein the at least on resilient element (9) is dimensioned relative to the hollow member (6) and the filler member (7) to seal the cavity inside the mixer shaft against fluids from the interior of the pouch (2).

13. The flexible pouch of claim 1, wherein the duct (10) connects the cavity inside the mixer shaft and a gas-filled headspace of the pouch (1) for pressure equalization.

14. The flexible pouch of claim 13, wherein the duct (2) is sealed off against fluids by a hydrophobic membrane permeable to gases and impermeable to microorganisms and cells.

15. The flexible pouch of claim 1, wherein each of the shaft elements is equipped with at least one stirring element.

* * * * *